United States Patent [19]

Rosen et al.

[11] Patent Number: 6,045,575
[45] Date of Patent: Apr. 4, 2000

[54] THERAPEUTIC METHOD AND INTERNALLY ILLUMINATED GARMENT FOR THE MANAGEMENT OF DISORDERS TREATABLE BY PHOTOTHERAPY

[75] Inventors: Danielle Rosen; Arye Rosen, both of Cherry Hill Township, Camden County, N.J.

[73] Assignee: AMT, Inc., Cherry Hill, N.J.

[21] Appl. No.: 09/015,226

[22] Filed: Jan. 29, 1998

Related U.S. Application Data

[60] Provisional application No. 60/058,469, Sep. 10, 1997.

[51] Int. Cl.[7] .................................................. A61B 17/36
[52] U.S. Cl. .............................. 607/88; 607/89; 606/3; 606/13; 219/211; 2/905; 362/32
[58] Field of Search ............... 606/9, 2, 14, 16, 606/10; 607/88, 89, 90, 108, 115; 219/211; 2/905

[56] References Cited

U.S. PATENT DOCUMENTS

| | | | |
|---|---|---|---|
| 3,729,613 | 4/1973 | Deloire et al. | 219/211 |
| 3,877,437 | 4/1975 | Maitan et al. | 607/88 |
| 4,055,166 | 10/1977 | Simpson et al. | 73/342 |
| 4,234,907 | 11/1980 | Daniel | 362/32 |
| 4,754,372 | 6/1988 | Harrison | 362/32 |
| 4,761,047 | 8/1988 | Mori | 350/96.1 |
| 4,851,816 | 7/1989 | Macias et al. | 340/573 |
| 4,907,132 | 3/1990 | Parker | 362/32 |
| 5,018,521 | 5/1991 | Campbell | 607/98 |
| 5,105,067 | 4/1992 | Brekkestran et al. | 219/497 |
| 5,339,223 | 8/1994 | Kremeachugsky et al. | 362/32 |
| 5,358,503 | 10/1994 | Bertwell et al. | 606/9 |
| 5,371,657 | 12/1994 | Wiscombe | 362/103 |
| 5,400,425 | 3/1995 | Nicholas et al. | 385/76 |
| 5,616,140 | 4/1997 | Prescolt | 606/10 |
| 5,698,866 | 12/1997 | Doiron et al. | 257/99 |
| 5,792,214 | 8/1998 | Larsson et al. | 607/88 |
| 5,800,479 | 9/1998 | Thiberg | 607/88 |
| 5,883,740 | 3/1999 | Chubb et al. | 2/125 X |
| 5,913,883 | 6/1999 | Alexander et al. | 607/88 |

*Primary Examiner*—Linda C. M. Dvorak
*Assistant Examiner*—Soju Harris-Ogugua
*Attorney, Agent, or Firm*—William H. Meise

[57] ABSTRACT

An apparatus for treating neonatal jaundice is in the form of a garment (10, 40) which has semiconductor light sources (14, 214, 314) affixed thereto for radiating toward the "inside" of the garment when the infant is dressed in the garment. A portable energy source such as batteries (318) or a fuel cell (360) powers the array of light sources. A method according to the invention vests the infant in the garment, and energizes the light sources by coupling a battery to the light sources, or fueling and starting the fuel cell. The therapy is continued for as long as desired or needed.

4 Claims, 4 Drawing Sheets

THERAPEUTIC METHOD AND INTERNALLY ILLUMINATED GARMENT FOR THE MANAGEMENT OF DISORDERS TREATABLE BY PHOTOTHERAPY

This application claims the benefit of the filing date of U.S. Provisional Patent Application Ser. No. 60/058,469 filed Sep. 10, 1997.

FIELD OF THE INVENTION

This invention relates to methods and apparatuses for medical treatment, and more particularly to the treatment of phototherapy-treatable disorders, such as jaundice.

BACKGROUND OF THE INVENTION

Hyperbilirubinemia (jaundice) is common in infants, and affects, in some degree, up to 50% of full-term infants, and most preterm infants. Bilirubin is the end result of chemical reactions involved in the breakdown of hemoglobin molecules. Bilirubin circulates through the blood stream chiefly in unconjugated form, and is processed by catalysis in the liver for conversion into a water-soluble form, which can then be excreted into the intestines as bile. The livers of newborn infants tend to have limited ability to process bilirubin, so infants are prone to accumulation of unconjugated bilirubin, and thus develop jaundice. In most cases, the jaundice is mild, and resolves spontaneously during the first week of life. However, jaundice is potentially dangerous, as high levels of bilirubin are toxic to brain tissue.

While the immaturity of liver cells is the chief cause of jaundice, there may be pathologic causes, which include hæmolytic anemia, polycythemia, extravasated blood, and even metabolic disorders. These pathologic causes can create sudden and severe onset of excess bilirubin levels. The goal of medical intervention is to mitigate or curtail the rise in bilirubin levels in the blood, to avoid a toxic accumulation. Approximately 10% of newborns require such intervention.

It is well known that, when infants are exposed to light in the blue region of the spectrum (410 to 460 nanometers or nm), a photochemical reaction takes place in the skin. The photochemical reaction changes unconjugated bilirubin into more soluble metabolites, including photobilirubin, which is then excreted into the bile, and if further photooxidation occurs prior to excretion, generates products which are excreted in the urine. Such phototherapy has proven to be an effective treatment for the vast majority of infants with unconjugated hyperbilirbinemia.

Infant phototherapy for jaundice is generally administered by phototherapy units, the effectiveness of which depend, at least in part, on the irradiance delivered by the light source, and the amount of skin exposed to the light. The light delivery systems in common use in hospital settings fall into two general categories, the first of which involves a crib-like structure for holding the infant, surmounted by banks of fluorescent or halogen lamps. These systems deliver light in the abovementioned blue region of the spectrum, at the target intensity of 5 to 9 $\mu W/cm^2/nm$ of bandwidth. This type of phototherapy unit has a number of disadvantages. First, the target light intensity is at a level at which retinal damage is of concern, and consequently the infant must wear protective eye patches. Secondly, to maximize the area exposed to the phototherapy, the infants must be essentially naked; since such infants have difficulty in temperature regulation, they must be maintained in temperature-controlled isolettes during phototherapy. Maintenance in temperature-controlled isolettes, in turn, tends to reduce the availability of human contact. The bulk and cost of the isolettes, in turn, tends to limit the use of this first type of phototherapy unit to hospital environments.

The second type of phototherapy unit which is generally available is the fiberoptic phototherapy blanket. This is a relatively flexible panel-like support for holding the ends of the fibers of one or more fiberoptic cables adjacent to a surface of the blanket, so that light propagating through the optical fibers is directed toward one side of the panel. This phototherapy blanket can be placed on the bottom of a conventional isolette, so that the infant can be illuminated from the bottom, as well as from the top by fluorescent or halogen lamps conventionally disposed. For infants with milder degrees of hyperbilirubinemia, the fiberoptic phototherapy blanket may be used alone, by wrapping the flexible panel about the infant's body, and securing the panel in place. Since the panel is opaque, there is less concern that the light can affect the infant's eyes, which tends to reduce the need for eye protection. If the panel is wrapped about the torso, the child can be dressed over the panel to keep it warm, and thus attains at least some mobility, which allows parental interaction, albeit limited by the "umbilical" optical fiber cable tethered to the light source. Since such phototherapy blanket units are relatively compact, they are more amenable to home use than the more conventional phototherapy "cribs". The ability to provide home therapy for mild cases of jaundice tends to reduce healthcare costs by eliminating the need for hospitalization in all but severe cases of jaundice.

Improved phototherapy devices and methods are desired.

SUMMARY OF THE INVENTION

The fiberoptic phototherapy blankets, while significant improvements over the crib-type units, have some disadvantages, namely that the infants being treated are treated only over limited regions of the body, namely the torso or trunk. Also, while the infant may be treated at home, the infant is effectively fixed in location to a selected room, because of the short length of the fiberoptic cable, and because of the need for a powerful light source for driving the light-source end of the fiberoptic cable, which in turn requires access to the AC power mains. Yet further, the halogen bulbs ordinarily used to drive fiberoptic cables have a life rated at 1000 hours, which is about 40 days, and the bulbs have a cost near $40.00 each.

In accordance with an aspect of the invention, a garment comprises a flexible support material shaped so as to be worn adjacent to the skin of at least a portion of the wearer's body. In various embodiments of the invention, the garment is in the shape of an infant jumpsuit, gown, shirt, or blanket. A plurality of semiconductor or solid-state light sources is affixed to the support material of the garment in such a manner that, when energized, each of the light sources radiates toward the skin of the wearer's body. In the context of a blanket-shaped garment, the light sources radiate from one of the two principal broad surfaces of the blanket. An energization coupler is coupled to the light sources, for coupling electrical energization to the light sources. In response to the electrical energization coupled to the light sources, the skin of the wearer of the garment is illuminated by the light sources.

In a particular embodiment of the invention, the garment is dimensioned to be worn by an infant, and the light sources radiate at least within a portion of the spectral range of 410 to 460 nanometers. In another embodiment, the energization coupler includes a source of electrical energy affixed to the garment. The source of electrical energy may include a battery or fuel cell. While not mandatory, the support material may be opaque, to avoid the possibility of affecting the eyes.

A method for treating an infant for jaundice, in accordance with an aspect of the invention includes the steps of dressing the infant or patient in the garment referred to above, energizing the light sources, and maintaining the unit energized for the desired length of time. The energizing step may include the placement of a battery in a battery holder affixed to the garment.

BRIEF DESCRIPTION OF THE DRAWING

FIG. 2b is a cross-section of the portion of FIG. 2a;

DESCRIPTION OF THE INVENTION

Figure 1A:
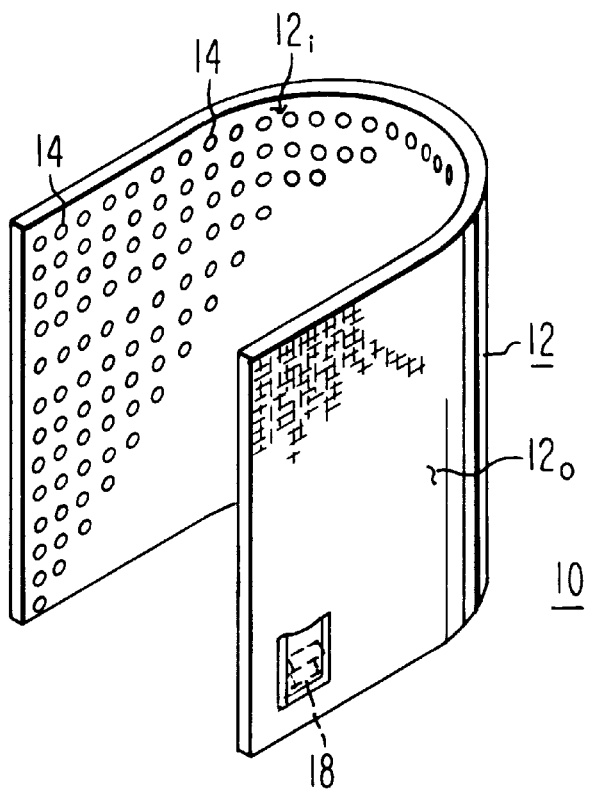
FIG. 1a is a simplified perspective or isometric view of a phototherapy blanket.

In FIG. 1a, a blanket-like garment designated generally as 10 includes a flexible support material 12, which may be, for example, a polymeric fabric, defining a first broad side 12o, which is designated as the "outside" when the garment 10 is worn, and also defining a second broad side 12i, which is the "inside". The blanket garment 10 of FIG. 1a also includes a plurality of semiconductor or solid-state light sources mounted thereon, with their radiating apertures, some of which are designated 14, opened or exposed to the inside surface 12i, so that when the semiconductor light sources are energized, radiation is from the inside surface 12i. The direction of radiation from each of the semiconductor light sources emitting apertures 14 is preferably more-or-less orthogonal to the local surface. Garment 10 of FIG. 1a also bears a portable energy source, which is illustrated as 18. In the case of FIG. 1a, energy source 18 includes a battery holder for holding one or more dry cells. Electrical conductors, not illustrated in FIG. 1a, extend from the source 18 to the semiconductor light sources, for providing energization thereto, as detailed below. When the semiconductor light sources are energized, they emit light, at least some of which lies in the range of 410 to 460 nanometers (nm).

Figure 1B:
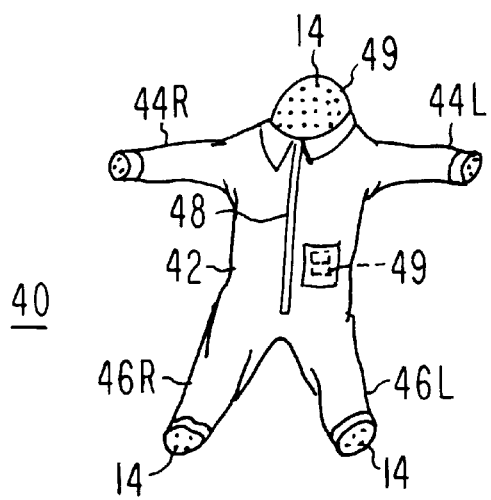
FIG. 1b is a simplified view of a garment according to aspects of the invention, in the form of an infant jumpsuit.

FIG. 1b illustrates a jump-suit-like garment 40, which has a neck opening 41, a torso portion 42 openable by means of a zipper 48, right and left arm portions 44R and 44L, and right and left leg portions 46R and 46L. A high rear collar portion 49 extends above the neck opening 41. The interior surfaces of the jump-suit garment 40 of FIG. 1b carries an array of emitters 14 of semiconductor light sources, which are interconnected (by electrical conductors, not illustrated in FIG. 1b) with a battery holder 49. When one or more batteries are inserted into holder 49, the semiconductor light sources 14 of garment 40 are illuminated, and radiate light, at least some of which lies in the range of 410 to 460 nm.

FIG. 2c represents an infant garment similar to that of FIG. 2, but in which the individual leg portions 46R and 46L are dispensed with, and an all-encompassing gown bottom 50, either open or closed, is substituted therefor.

Figure 1C:
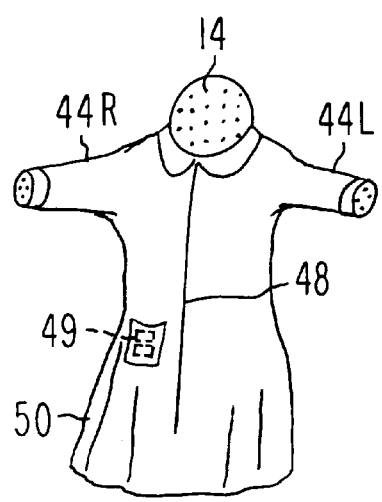
FIG. 1c is a simplified view of an infant garment in the form of a gown.
Figure 2A:
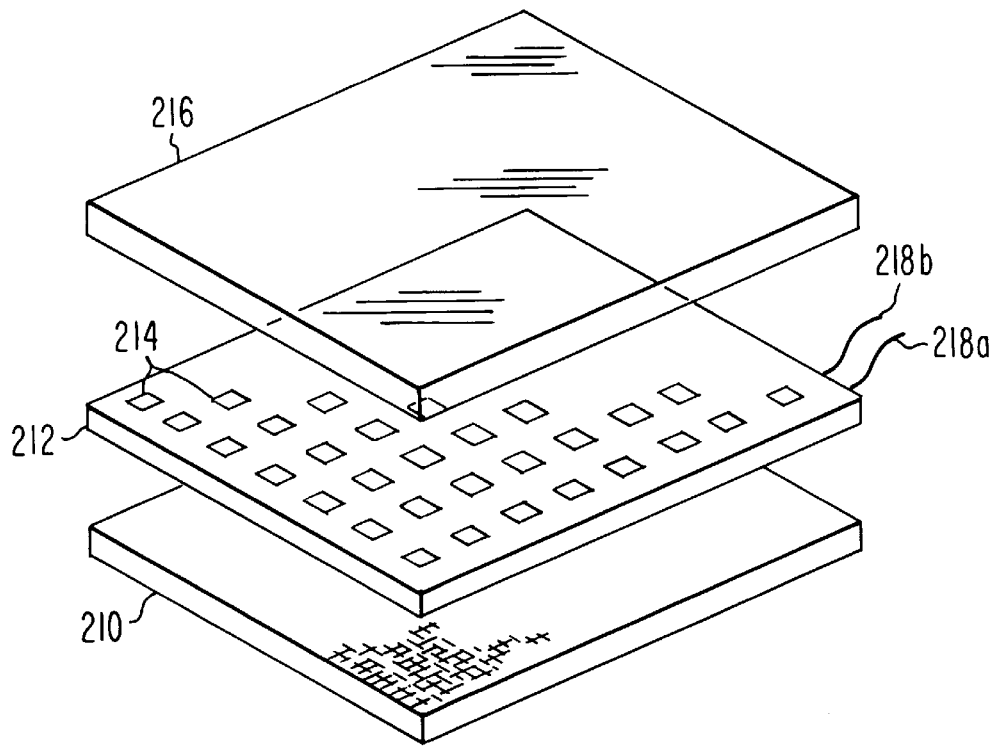
FIG. 2a is a detailed view of a portion of one side of the blanket of FIG. 1a, which is the same as a detailed view of a portion of the interior of the jumpsuit of FIG. 1b, exploded to illustrate the various layers.
Figure 2B:
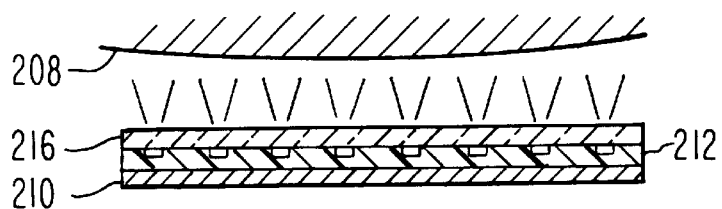

FIG. 2a is an exploded, perspective or isometric view of a portion of the material of the garment of FIG. 1a, 1b, or 1c, showing the various layers of the material, and how they interrelate. FIG. 2b is a cross-section of the portion of the material of FIG. 2a in its combined form. In FIGS. 2a and 2b, the flexible mechanical support fabric is illustrated as a layer 210. A layer 212 represents a thin, flexible, dielectric sheet, on the upper surface of which are mounted the various semiconductor light sources 214 of an array of light sources. The dielectric sheet also carries the electrical conductors which connect to the semiconductor light sources, and which also connect to flexible connection wires 218a and 218b, which ultimately make electrical connection to the battery holder 18 or 49 of FIGS. 1a and 1b, respectively. The semiconductor light sources 214 are mounted on the sheet 212 in a manner which allows their light radiation to be directed upward.

Those skilled in the art of semiconductor light sources know that their radiation may subtend a small solid angle, or in other words that they may produce sharply directive beams of light. It may be desirable to diffuse the light from the semiconductor light sources 214. This could be accomplished by affixing a diffusing lens to each of the semiconductor light sources 214. Instead, in the arrangement of FIGS. 2a and 2b, a further layer 216 of transparent fabric, such as woven NYLON, is placed over dielectric layer 212. The fibers of the transparent fabric 216 are in the form of cylinders, which is one form which diffusing lenses can take, and the fabric therefore acts to diffuse the light from the semiconductor light sources, and tends to spread it over the adjacent surface of the body being treated. The transparent fabric also prevents direct contact of the skin of the patient with the semiconductor light sources 214 or with the dielectric sheet 212.

Figure 3A:
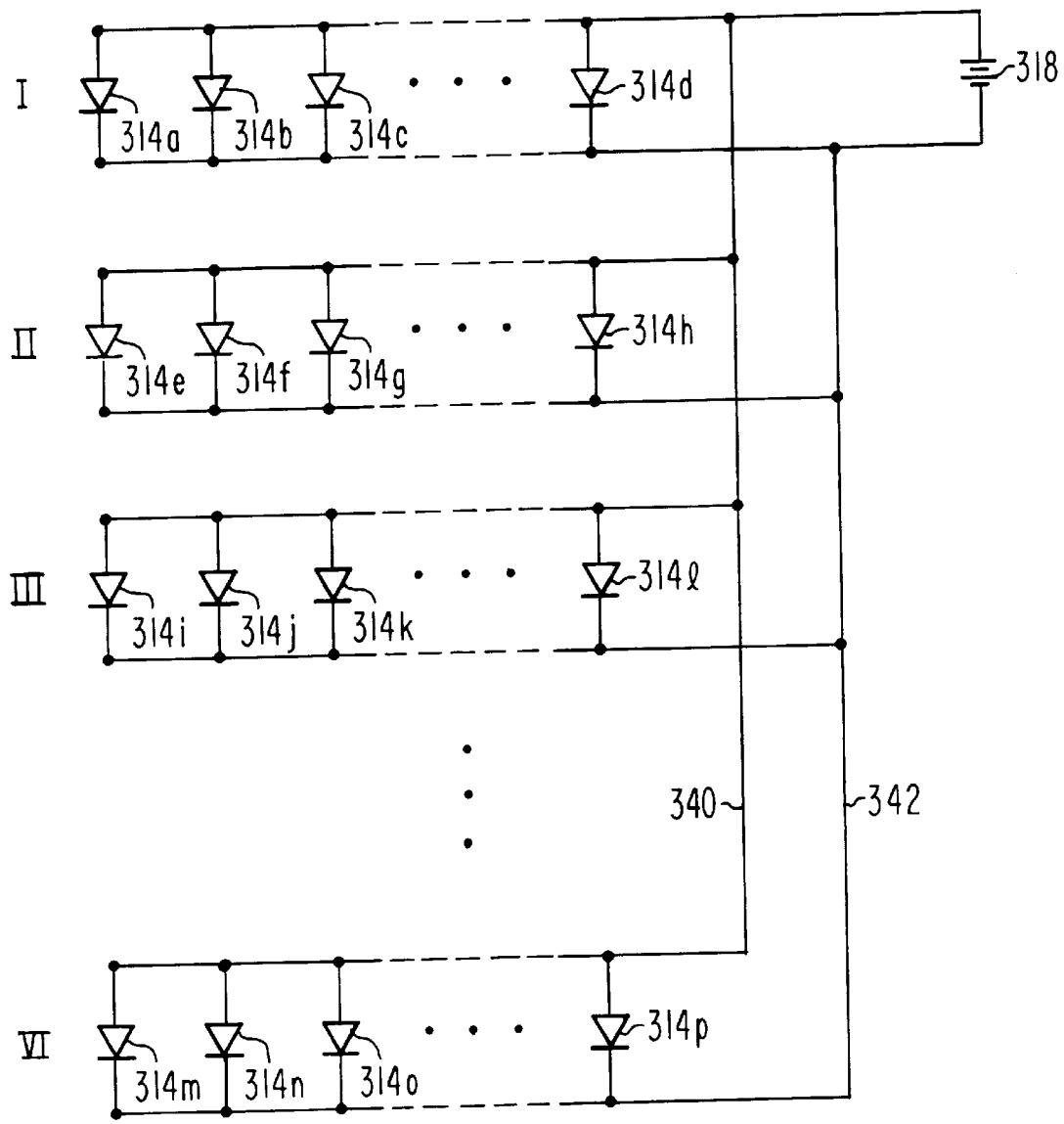
FIG. 3a illustrates how the semiconductor light sources of the invention may be electrically coupled in parallel for energization by a low-voltage-source.

FIG. 3a illustrates one type of electrical connection which can be made between a battery 318 and an array of semiconductor light sources, illustrated by diode symbols. As illustrated therein, the light sources 314a, 314b, 314c, . . . 314d are arranged in a first row I, light sources 314e, 314f, 314g, . . . 314h are arranged in a second row II, light sources 314i, 314j, 314k, . . . 314l are arranged in a third row III, and light sources 314m, 314n, 314o, . . . 314p are arranged in a last row designated VI. Electrical conductor 340 connects the "anodes" of all of the light sources 314 to the positive terminal of battery 318, while the electrical conductor 342 connects the "cathodes" of all of the light sources 314 to the negative terminal of the battery. With this arrangement, the battery voltage appears across each of the light sources.

Figure 3B:
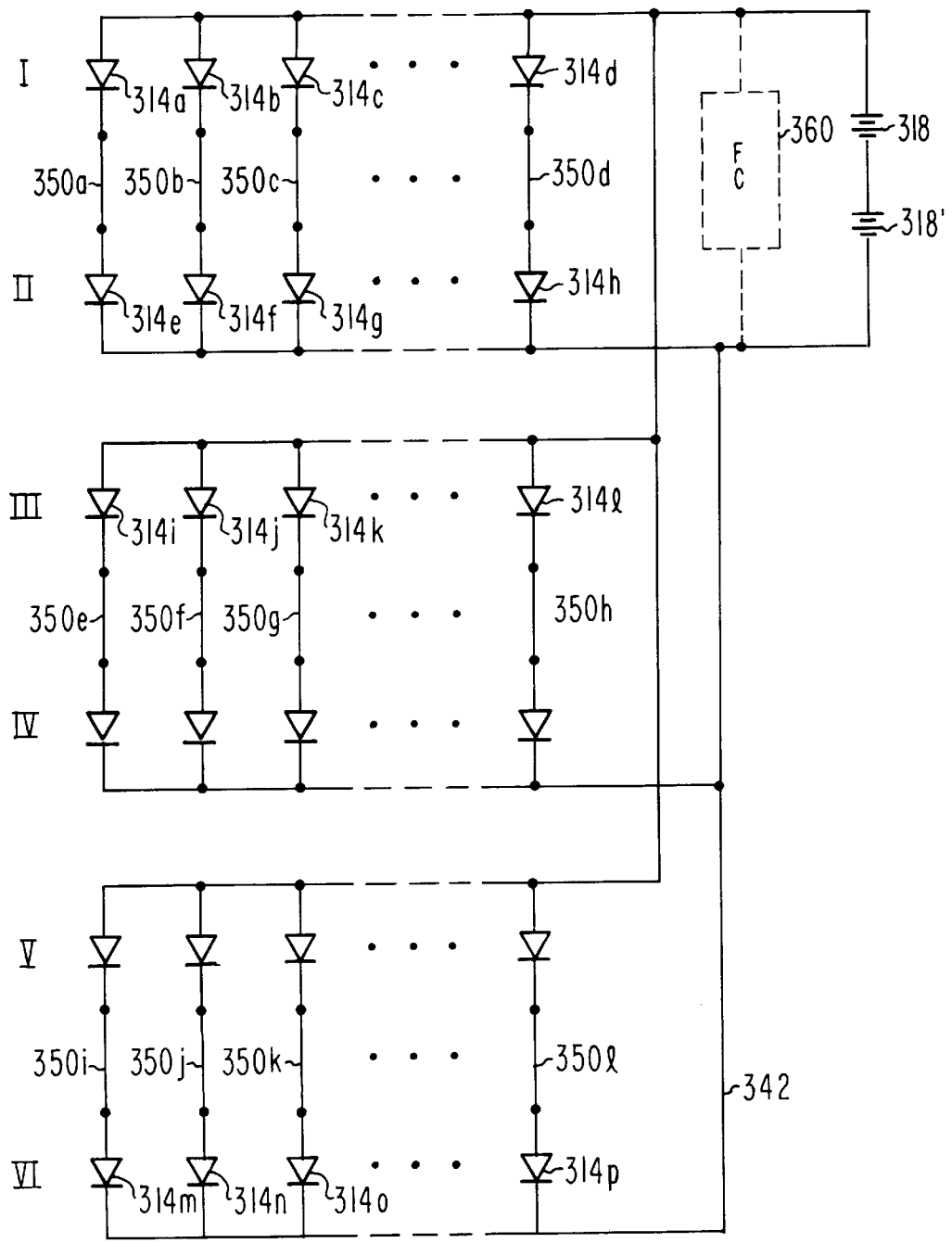
FIG. 3b illustrates how the semiconductor light sources can be coupled in series-parallel for operation from higher voltage sources.

FIG. 3b illustrates another type of electrical connection which can be made among the light sources 314 and the battery 318. In the arrangement of FIG. 3b, elements corresponding to those of FIG. 3a are designated by like reference numerals. In FIG. 3b, additional rows IV and V of semiconductor light sources are illustrated. Conductor 340 is connected to the "anodes" of the light sources of rows I, III, and V, while conductor 342 is connected to the "cathodes" of the light sources of rows II, IV, and VI. In addition, a set of electrical conductors 350a, 350b, 350c, . . . 350c individually connects the "cathodes" of light sources 314a, 314b, 314c, . . . , 314d to the "anodes" of light sources 314e, 314f, 314g, . . . , 314h, respectively. A further set of electrical conductors 350e, 350f, 350g, . . . 350h individually connects the "cathodes" of light sources 314i, 314j, 314k, . . . , 314l to the "anodes" of the light sources (not individually designated) of row IV. Similarly, a further set of electrical conductors 350*i*, 350*j*, 350*k*, . . . , 350*l* individually connects the "cathodes" of the semiconductor light sources of row V to the "anodes" of the light sources 314*m*, 314*n*, 314*o*, . . . , 314*p* of row VI. Those skilled in the art will recognize this as a series-parallel electrical connection, which requires less total current from the electrical source, but, for equal power, requires double the applied voltage. In the arrangement of FIG. 3*b*, the additional voltage is represented by an additional battery designated 318', illustrated as being connected in series with battery 318. Those skilled in the art know that many different series-parallel connections are possible, to achieve almost any desired ratio of energization voltage to current. The selected ratio should be suited to the capabilities of the source of voltage, which in the illustrated arrangement is a battery. Instead of a battery as illustrated in FIG. 3*b*, the energization source could be a fuel cell, illustrated in dashed lines as 360.

It should be understood that, when a jumpsuit garment is to be used, that the light sources in the various parts of the garment, such as the right and left arms, the torso portion, and the like, must be connected together on their portion, and then the individual portions must be electrically interconnected after the individual portions are sewn or otherwise bonded together to form the garment.

Other embodiments of the invention will be apparent to those skilled in the art. For example, while the batteries have been indicated as being dry cells, wet cells can be used. The electrical conductors which interconnect the light sources and the energy source may be located on a surface of the garment, so long as appropriately insulated, or within the support material of the garment. While not explicitly illustrated, the garment according to the invention may also carry switches or other devices for controlling the flow of current to the light sources. While the jumpsuit garment 40 of FIG. 1*b* as illustrated does not have integral feet, it will be understood that feet are advantageous, in that covering the feet tends to keep the infant warmer, and extending the array of semiconductor light sources into the feet allows the region of the phototherapy to encompass the feet of the infant, as well as the other portions covered by the jumpsuit garment.

Thus, a garment (10, 40) according to an aspect of the invention comprises a flexible support material (12, 210) shaped so as to be worn adjacent to the skin (208) of at least a portion of the wearer's body. In one embodiment of the invention, the garment (10, 40) is in the shape of a blanket (FIG. 1*a*), and in another embodiment, the garment (10, 40) is in the shape of an infant jumpsuit (FIG. 1*b*). A plurality of semiconductor light sources (14, 214, 314), such as lasers or light-emitting diodes, are affixed to the support material (12, 210) of the garment (10, 40) in such a manner that, when energized, each of the light sources (14, 214, 314) radiates toward the skin (208) of the wearer's body. In the context of a blanket-shaped garment (10, 40), the light sources (14, 214, 314) radiate from one (12*i*) of the two principal broad surfaces (12*i*, 12*o*) of the blanket (FIG. 1*a*). An energization coupler (18) is coupled to the light sources (14, 214, 314), for coupling electrical energization to the light sources (14, 214, 314). In response to the electrical energization coupled to the light sources (14, 214, 314), the skin (208) of the wearer of the garment (10, 40) is illuminated by the light sources (14, 214, 314) (20). In one embodiment of the garment, a layer of light-diffusing material (216) is placed adjacent to the light sources ((214) on that side of the light sources remote from their support material (210).

In a particular embodiment of the invention, the garment (10, 40) is dimensioned to be worn by an infant, and the light sources (14, 214, 314) radiate at least within a portion of the spectral range of 410 to 460 nanometers. In another embodiment, the energization coupler includes a source (18) of electrical energy affixed to the garment (10, 40). The source (18) of electrical energy may include a battery (318, 318') or fuel cell (360). The support material (12, 210) may be opaque, to avoid the possibility of affecting the eyes.

A method for treating an infant for jaundice, in accordance with an aspect of the invention includes the steps of dressing the infant or patient in the garment (10, 40) referred to above, energizing the light sources (14, 214, 314), and maintaining the unit energized for the desired length of time. The energizing step may include the placement of a battery (318, 318') in a battery holder (18) affixed to the garment (10, 40).

What is claimed is:

1. A garment, comprising:

a flexible support material shaped so as to be worn adjacent to the skin of at least a portion of the wearer's body:

a plurality of semiconductor light sources affixed to said support material in such a manner that, when energized, each of said light sources radiates toward said skin of said wearer's body; and energization coupling means coupled to said light sources, for coupling electrical energization to said light sources, whereby, when said electrical energization is coupled to said light sources, said skin of said wearer is illuminated by said light sources, further comprising a layer of light-diffusing material located adjacent said light sources and remote from said support material.

2. A method for treating an infant for jaundice, comprising the steps of:

dressing said infant in a garment comprising
(a) a flexible support material shaped so as to be worn adjacent to the skin of at least a portion of the infant's body:
(b) a plurality of semiconductor light sources affixed to said support material in such a manner that, when energized, each of said light sources radiates at a wavelength within the range of 410 to 460 nanometers toward said skin of said infant's body; and
(c) energization coupling means coupled to said light sources, for coupling electrical energization to said light sources;

coupling a source of electrical energy to said energization coupling means, for thereby energizing said semiconductor light sources; and maintaining said light sources energized for a selected time period.

3. A method according to claim 2, for use when said garment is in the shape of a blanket, wherein said step of dressing includes the step of wrapping at least a portion of said infant in said blanket-shaped garment.

4. A method according to claim 2, wherein said step of coupling a source of electrical energy includes the step of inserting a battery into a battery holder associated with said garment.

* * * * *